United States Patent [19]

Jacobus et al.

[11] 4,058,624

[45] Nov. 15, 1977

[54] BROAD SPECTRUM ANTIBACTERIAL COMPOSITIONS CONTAINING TRIS (HYDROXYMETHYL)-AMINOMETHANE AND DIPHENYL AND LOWERALKYL SUBSTITUTED DIPHENYL POLYAMINES

[75] Inventors: David P. Jacobus, Princeton; Eugene L. Dulaney, Summit; Nathaniel Grier, Englewood, all of N.J.

[73] Assignee: Merck & Co., Inc., Rahway, N.J.

[21] Appl. No.: 686,360

[22] Filed: May 14, 1976

[51] Int. Cl.$^2$ .......................... A01N 9/02; A01N 9/20; A01N 9/22

[52] U.S. Cl. .......................... 424/330; 260/570.5 P; 260/570.6; 424/250; 424/325

[58] Field of Search ................ 71/67; 424/250, 325, 424/330; 260/570.5 P, 570.6

[56] References Cited

U.S. PATENT DOCUMENTS

| | | | |
|---|---|---|---|
| 2,483,434 | 10/1949 | Rieveschl, Jr. ........................ | 260/570 |
| 2,781,398 | 2/1957 | Morren ............................... | 260/570.5 |
| 3,064,052 | 11/1962 | Goldberg et al. .................... | 260/563 |
| 3,197,510 | 7/1965 | Cyba .................................. | 260/584 |
| 3,466,162 | 9/1969 | Gloor et al. ......................... | 71/67 |
| 3,823,155 | 7/1974 | van der Stelt ...................... | 260/309.6 |
| 3,862,330 | 1/1975 | Johnson et al. ..................... | 424/330 |
| 3,874,869 | 4/1975 | Koppensteiner et al. ............. | 71/67 |
| 3,876,702 | 4/1975 | Petersen et al. .................... | 260/570 R |
| 3,900,565 | 8/1975 | Grisar et al. ........................ | 424/274 |

FOREIGN PATENT DOCUMENTS

| | | |
|---|---|---|
| 461,817 | 12/1970 | Australia |
| 810,291 | 11/1973 | Belgium |

OTHER PUBLICATIONS

Voss, Journal General Microbiology, 48, 391–400 (1967).

*Primary Examiner*—Allen J. Robinson
*Attorney, Agent, or Firm*—Edmunde D. Riedl; Julian S. Levitt

[57] ABSTRACT

A composition comprising tris-(hydroxymethyl)aminomethane and diphenyl and loweralkyl substituted diphenyl polyamines, their acid addition salts, and mixtures thereof are useful as antibacterial agents. The composition is particularly useful because of the synergistic improvement obtained against strains of the genus Pseudomonas, as well as other genera.

9 Claims, No Drawings

BROAD SPECTRUM ANTIBACTERIAL COMPOSITIONS CONTAINING TRIS (HYDROXYMETHYL)-AMINOMETHANE AND DIPHENYL AND LOWERALKYL SUBSTITUTED DIPHENYL POLYAMINES

DISCLOSURE OF THE INVENTION

This invention relates to antibacterial compositions. More particularly, this invention relates to compositions comprising an admixture of tris-(hydroxymethyl)aminomethane and either individually or in combination a polyamine having the structural formula:

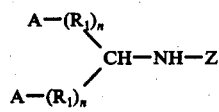   (I)

where:
each A is alike or different and is

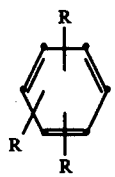

each R is alike or different and is hydrogen or loweralkyl;
Each $n$ is alike or different and is the integer 0 or 1;
Each $R_1$ is alike or different and is $C_1$ to $C_4$ alkylene;
Z is

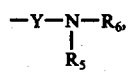

where
Y is

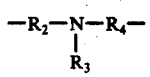

or Y is $R_2$
and $R_2$ is 2-hydroxy-1,3-trimethylene, or $R_1$ as previously defined;
$R_3$ is hydrogen, $C_1$ to $C_4$ alkyl, $C_2$ to $C_4$ aminoalkyl or $C_1$ to $C_4$ hydroxyalkyl, $C_2$ to $C_4$ dihydroxyalkyl, e.g., 2,3-dihydroxypropyl and 3,4-dihydroxybutyl; and
$R_4$ is 2-hydroxy-1,3-trimethylene, or $R_1$ as previously defined;
$R_5$ is hydrogen, aminoethyl, aminopropyl, $C_1$ to $C_4$ hydroxyalkyl, or $C_2$ to $C_4$ dihydroxyalkyl; and
$R_6$ is hydrogen, $C_1$ to $C_4$ hydroxyalkyl or $C_2$ to $C_4$ dihydroxyalkyl;
or when $R_3$ and $R_6$ taken together are ethylene, $R_4$ is also ethylene, and $R_5$ is aminoethyl, aminopropyl, or aminohydroxypropyl;
and optionally their acid addition salts particularly the hydrochloride.

The antibacterial composition comprises at least 0.5 part by weight of the tris-(hydroxymethyl)aminomethane for each part by weight of the polyamine expressed as the base compound, and more preferably from 1 to 500 parts of the tris-(hydroxymethyl)aminomethane. Generally, the combination of trisamine and polyamine is combined in a suitable solvent or dispersant as a carrier. Such solvents or dispersants, for example, are usually polar and those such as water, lower alkylene glycol, or lower alkanols including amyl alcohol are especially suitable as well as in mixtures of such solvents. Such inclusion of the antibacterial combination in a suitable solvent is not required to produce the synergistic action, but is merely a convenience when using the combination as an antibacterial agent. In fact, an excess of tris-(hydroxymethyl)aminomethane can conveniently be employed as an admixture with salts of the polyamines in powders, suspensions, or solutions.

In formulations including the synergistic composition of this invention, it is suitable to include other antibacterial agents, suspending agents, wetting agents, antiscaling agents, corrosion inhibitors, and pH control agents such as the usual buffers commonly employed to achieve a desired pH. Therefore, alkali silicates, alkali phosphates, alkali gluconates, polyphosphates, and pyrophosphates, organic amines, polyamines, and polyamides; anionic, cationic and non-ionic wetting agents; alkali carbonates, bicarbonates, sulfates, sesquicarbonates; and the like can suitably be included in the final formulation.

In use, the antibacterial composition can be applied as a rinse, a drench, or if employed as a cleanser for skin can be used as a soap, a cream, or a foaming composition. If desired, the material can also be packaged in aerosol form and sprayed on surfaces where antibacterial control is desired. In addition, the material can be used to impregnate fabrics, woven or nonwoven to render them bacteriostatic.

One especially desirable application is its use in floor and wall cleaning formulations wherein the antibacterial composition, preferably including also pH control agents, wetting agents, and those other agents that are commonly found in floor cleaning formulations is further diluted with water and applied by mopping, swabbing or other conventional means.

Acid addition salts of one or more amino functions of the triazaalkane or tetraazaalkane moiety of the polyamine can be employed. Suitable anions for the salt include anions derived from inorganic acids as well as those of organic acids such, for example, as halide, i.e., chloride, bromide or iodide or sulfate, nitrate, bisulfate, phosphate, acetate, propionate, maleate, succinate, laurate, palmitate, oleate, stearate, ascorbate, gluconate, citrate, carbonate, bicarbonate, benzoate, salicylate, pamoate, phthalate, furoate, picolinate, dodecylbenzenesulfonate, laurylethersulfate, nicotinate and the like. Generally, any anion derived from an acid is suitable and satisfactory when the polyamine salt anion, for example, the chloride is replaced with other anions, by well known anion exchange techniques. Most suitably, the chloride salt is passed through an anion exchange resin.

In a preferred embodiment of this invention, an antimicrobial composition of polyamine, e.g., 1-[1,5-di-(t-butylphenyl)-3-pentyl]-1,5,9-triazanonane trihydrochloride admixed with tris(hydroxymethyl)aminomethane provides upon solution in aqueous media a concentration of 1-100 ppm of polyamine salt and 1000–5000 ppm of tris(hydroxymethyl)aminomethane. Whereas the polyamine salt by itself is capable of inhibiting gram negative and gram positive bacteria at such dilutions, various strains of Pseudomonas appear unaffected. In the presence of the tris(hydroxymethyl)aminomethane they are controlled by the polyamine even at its lower concentration range. Moreover, only about one-half to one-tenth the inhibitory concentrations of polyamine is needed in combination to suppress *Pseudomonas aeruginosa* as compared to the polyamine alone.

The following examples show methods for preparing the polyamines of this invention as typical of those that can be used in applications employing the synergistic composition of this invention.

The compounds of this invention are preferably prepared according to the following sequence of reactions:

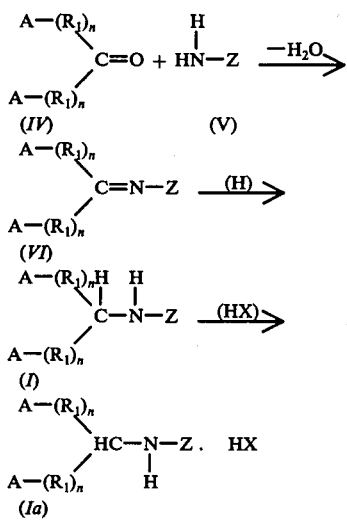

where A, z and n have their previously defined meanings, HX is a mono or polybasic organic or inorganic acid, where sufficient HX is provided to protonate at least one amino group of phenyl polyamine compound I, to form salt I(a).

The preparation of phenyl polyamine I comprises the Schiff base reaction of the appropriate ketone IV and the appropriate amine V.

If amine V has two primary amino groups, it can either be symmetrical or unsymmetrical. An amine V, which is a symmetrical amine, e.g., where $R_2$ and $R_4$ are alike when $R_5$ and $R_6$ are hydrogen forms a single Schiff base VI. This is because regardless of which terminal primary amine group of amine V reacts with ketone IV, the same product results. However, where amine V is unsymmetrical at least two products can result. For example, if Y is

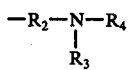

and $R_5$ is either aminoethyl or aminopropyl, there is obtained Schiff base VI

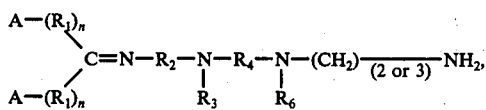

as well as Schiff base VI(a)

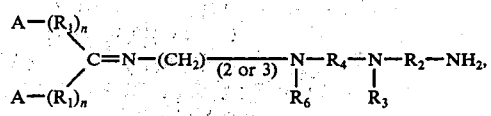

where A, $R_{1-6}$ and n are as previously defined. Note that both products VI and VI(a) come within the scope of the definition given for Schiff base VI. Where multiple products such as Schiff bases of formulas VI and VI(a) are produced, they can be separated, if desired, by the usual and well known separation techniques, i.e., distillation and the like.

As an alternative to obtaining a mixture of Schiff bases VI and VI(a) or VI(b), which upon reduction give a mixture of product I the reaction can be conducted stepwise. For example, 1,4-diaminobutane or 4-(2-aminoethyl)piperazine may be converted to a Schiff base with 1,5-di-(4-isopropyl)-phenyl)-3-pentanone, catalytically reduced, then the resulting amine selectively cyanoethylated with acrylonitrile, followed by catalytic hydrogenation to furnish 1-(3-aminopropyl)-4-[1,5-di-(4-isopropylphenyl)-3-pentyl]diaminobutane, a spermidine derivative, or 1-(3-aminopropyl)-4-[2-{(1,5-di-(4-isopropylphenyl)-3-pentylamino}ethyl]piperazine. A primary amine can be dicyanoethylated with excess acrylonitrile, catalytically reduced to the corresponding 3,3'-substituted iminobis(propylamine) and then converted by condensation with a ketone and reduction to the N-alkylated-3,3'-substituted iminobis(proylamine). For example, dicyanoethylation of monoethanolamine followed by catalytic reduction provides 3,3'-(2-hydroxyethylimino)bis(propylamine). Condensation with 1-(2,4-dimethylphenyl)-6-(3-isopropylphenyl)-3-hexanone and subsequent catalytic hydrogenation of the —C=N bond affords 1-[1-(2,4-dimethylphenyl)-6-(3-isopropylphenyl)-3-hexyl]-5-(2-hydroxyethyl)-1,5,9-triazanonane.

To prepare Schiff base VI, ketone IV and amine V are dissolved in a suitable inert solvent, for example, toluene, and heated to reflux, until reaction is substantially complete. Usually 5 to 20 hours is sufficient for water removal by azeotropic distillation. The solvent is then removed under reduced pressure and the residue comprising the Schiff base VI is dissolved in an inert solvent preferably an alkanol, such as ethanol or isopropanol.

After dissolution, the Schiff base VI is catalytically or chemically reduced.

In catalytic reductions, hydrogen saturates an alkanol solution of Schiff base VI using agitation in the presence of the usual hydrogenation catalysts, such as transition metals and their reducible oxides. Especially effective catalysts are the noble metals and their oxides. A particularly preferred catalyst is platinum oxide. Generally, the hydrogenation reaction is carried out in a manner well known in the art. Small particles, e.g., 100-300 mesh of catalyst are admixed with the Schiff base and excess amine in alcohol and placed in a closed system pressurized with from 3-5 atmospheres of hydrogen gas. After reaction is complete, the pressure is released and the catalyst separated from the reaction mixture by filtration. The filtrate containing the phenyl polyamine I, is then further purified by usual techniques. Preferably, whatever solvent may be present is removed under reduced pressure, the residue then dissolved in a water-immiscible solvent, washed with water, followed by a further washing with a saturated aqueous inorganic salt solution. After drying, the solvent is removed by evaporation under reduced pressure giving the phenylpolyamine I usually as an oil. The phenylpolyamine can then be redissolved in loweralkanols, mixtures of loweralkanols and water, diethylether, dioxane and then neutralized with an acid, e.g., hydrogen chloride, or neutralized directly with aqueous acids.

Acid addition salts I(a) are then isolated, if desired, by precipitation, evaporation or other usually employed techniques.

Suitable anions X for the salt I(a) include anions derived from inorganic acids as well as those of organic acids such for example as halide, i.e., chloride, bromide or iodide or sulfate, nitrate, bisulfate, phosphate, acetate, propionate, maleate, succinate, laurate, palmitate, oleate, stearate, ascorbate, gluconate, citrate, carbonate, bicarbonate, benzoate, salicylate, pamoate, phthalate, furoate, picolinate, dodecylbenzenesulfonate, laurylethersulfate, nicotinate and the like. Generally, any anion derived from an acid is suitable and satisfactory when the polyamine salt anion $X^-$, e.g., chloride is replaced with other anions, by well known anion exchange techniques.

Alternatively, a chemical rather than a catalytic reduction is employed to reduce Schiff base VI to product I.

In this chemically reductive procedure, the ketone IV is reacted with the appropriate amine as before, but the Schiff base VI dissolved in an alkanol or inert ether-type solvent is reacted with a chemical reductant such as sodium borohydride or lithium aluminum hydride, respectively.

Although as little as an equivalent of the chemical reductant can be used successfully, most satisfactory results are obtained if at least two molar excess of and preferably at least a 2.5 molar excess of the chemical reductant is employed. After any initial reaction has subsided, the reaction mixture may be heated at reflux for an hour or two, then cooled to room temperature, and afterwards concentrated under vacuum. The residue obtained is then further purified as by treatment with mineral acid or inorganic base as was described for polyamines I and the salt may thereafter be formed as previously described.

The diphenyl ketones IV are readily prepared and two alternative methods, are set forth below.

A. The Condensation of Acids - This method involves the following reaction scheme:

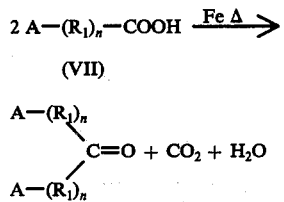

Acylative decarboxylation of acids VII is employed by heating the acid at elevated temperatures either with transition metals, preferably iron, transition metal oxides, alkaline earth oxides, with polyphosphoric acid or with boron trifluoride. Most suitably, acylative reaction is achieved by passage of acid vapors over catalysts such as heated thoria aerogel.

Condensation-decarboxylation of an acid is the preferred method for preparing ketone IV when each $A-(R_1)_n$ group is alike and $n=1$, a mixture of products being obtained when several different acids are combined in a reaction. The preferred reaction comprises admixing carboxylic acid VII with reduced iron powder and stirring in an inert atmosphere at 195° C. to 200° C. for 1-6 hours to form an iron salt.

Preferably, the carboxylic acid VII and iron are agitated under an inert atmosphere of nitrogen for at least 2 hours at 195° C. to 200° C.

After 2 hours, the temperature is increased suitably to 290° C. to 310° C. and agitation continued for at least another 3 hour period, 4 hours usually being sufficient. The reaction mixture is allowed to cool, and then is extracted with a suitable inert solvent such as diethylether and filtered. The solvent extracts are concentrated under reduced pressure. The residual liquid is distilled under vacuum to isolate the ketone IV.

The carboxylic acids VII employed above are prepared by various means well known in the art.

B. Condensation of a Grignard and a Nitrile

Diphenyl alkanones can be obtained according to the following reaction scheme:

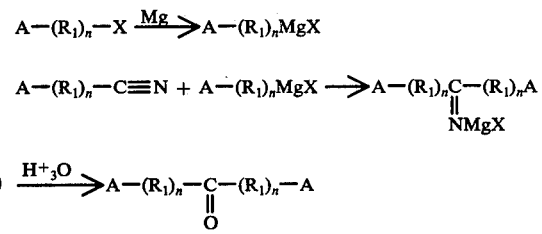

where A or $(R_1)_n$ of each reactant may be the same or different and are as previously defined.

This general procedure utilizes the reaction of a Grignard reagent prepared from a chloro- or bromo-substituted phenyl derivative with a cyanosubstituted phenyl derivative. The resultant disubstituted iminoalkane Grignard complex is hydrolyzed with aqueous mineral acid to the corresponding ketone.

The Grignard reagent is obtained by reaction of the halide with magnesium metal, usually in the form of turnings or powder and may be catalyzed by very small concentrations of iodine or methyl iodide. Solvents which are useful include diethyl ether, dibutyl ether, tetrahydrofuran, dioxane and benzene. Usually, gentle warming suffices to initiate the reaction and the halide is gradually added to the metal-solvent mixture. After complete addition the disappearance of practically all magnesium metal signifies the end of the reaction. A small excess of halide is used and moisture must be excluded; a nitrogen atmosphere is beneficial. The Grignard reagent is then added to the nitrile, which is previously dissolved in two or three times its volume of solvent, over a period of 15 minutes to 1 hour at ambient temperature. The reaction mixture may then be heated to reflux to insure complete reaction. Generally, a small excess of Grignard reagent as compared to nitrile is employed. From 1 to 10 hours at reflux is sufficient for complete conversion. The resultant imine salt is preferably decomposed and hydrolyzed to the ketone with aqueous mineral acids such as hydrochloric, sulfuric and phosphoric. The ketones are water-insoluble and may be extracted with water-immiscible solvents. Purification is preferably accomplished by fractional distillation under reduced pressure. It is feasible to use the crude ketone reaction mixture for the alkylation of polyamines as the Grignard reaction by-products are usually alcohols or hydrocarbons and do not react with amines. The reactant halides, if present in the crude product, should be removed prior to the ketone-amine alkylation process.

The concentrations of Grignard reagent and nitrile may be varied over wide limits for securing good yields in the process. The halide and cyano, as well as carboxylic derivatives of phenyl compounds, e.g., phenylacetic acid are readily available.

Once the ketone IV is obtained it can then be reacted with a suitable polyamine V. Polyamines V which are exceptionally suitable for reaction with ketone IV include diethylenetriamine, triethylenetetramine, 3,3-iminobis(propylamine), 3,3-methyliminobis-(propylamine), dipropylenetriamine, N,N'-bis-(3-aminopropyl)-1,3-trimethylenediamine, N,N'-bis-(2-aminoethyl)-1,3-trimethylenediamine, N,N'-bis(3-aminopropyl)piperazine, N-(3-amino-2-hydroxypropyl)-1,3-trimethylenediamine, N-(2-aminoethyl)-1,3-trimethylenediamine, spermidine, spermine, 1,4-bis-(2-aminoethyl)piperazine, tris-(2-aminoethyl)amine, 1-(2-aminoethyl)-4-(3-aminopropyl)piperazine, 1-(3-amino-2-hydroxypropyl)-4-(2-aminoethyl)piperazine, 1-(2,3-dihydroxypropyl)-1,5,9-triazanonane, 1-(2-hydroxyethyl)-1,4,7,10-tetraazadecane, 4-(3,4-dihydroxybutyl)-1,4,8-triazaoctane, 1-(2-hydroxypropyl)-5-hydroxymethyl-1,5,9-triazanonane, tris-(3-aminopropyl)amine, ethylenediamine, trimethylenediamine, and 1,3-diamino-2-hydroxypropane.

The compounds described herein are excellent broad spectrum antimicrobial agents which are especially effective against gram positive and negative bacteria, particularly troublesome gram-negative members of the genus Pseudomonas at aqueous concentrations of 1.0 to 100 ppm. Examples of susceptible species include, inter alia, *Staphylococcus aureus, Streptococcus pyrogenes, Bordetella bronchiseptica, Corynebacterium acnes, Pasteurella multocida, Escherichia coli, Salmonella typhimurium, S. pullorum, Klebsiella pneumoniae, Aerobacter aerogenes, Pseudomonas aeruginosa, Desulfovibrio desulfuricans, Bacillus mycoides,* fungi such as *Aspergillus niger* and *Chaetomium globosum* and yeast such as *Candida albicans.*

The low toxicity of these compounds makes them especially attractive for use where contact with skin surfaces or possible ingestion renders the use of irritating or toxic materials inadvisable. Exemplary toxicity of a representative number of compounds is tabulated in Table I below.

TABLE I

| Compound | Acute Toxicity Oral LD$_{50}$ mice |
|---|---|
| 1-[1,7-di-(2-methyl-5-t-butylphenyl)-4-heptyl]-1,5,9-triazanonane trihydrochloride | 1650 mg./kg. |
| 1-[1,7-di-(2-methyl-5-t-butylphenyl)-4-heptyl]-1,4,7,10-tetrazadecane tetrahydrochloride | 2070 mg./kg. |
| 1-[1,7-bis-(4-t-butylphenyl)-4-heptyl]-1,5,9,13-tetrazatridecane tetrahydrochloride | 1550 mg./kg. |
| 1-[1,5-di-(2,4,6-trimethylphenyl)-3-pentyl]-1,5,9-triazanonane trihydrochloride | 1150 mg./kg. |

PREPARATION A

Preparation of 1,5-Di-(4-Isopropylphenyl)-3-pentanone 3-(4-Isopropylphenyl)propionic acid (0.20 mole) and iron (hydrogen reduced, 6.15 g., 0.11 mole) are heated for 1.5 hours at 195° C. under a nitrogen atmosphere. After that time, the temperature is increased to 290° C. and maintained at that temperature for 3 hours. The cooled reaction mass is extracted well with ether, filtered through Celite, and the ethereal extracts concentrated under vacuum. The residue is stripped under vacuum to leave the product, 17.3 g. (51%).

In an analogous manner there are obtained the following ketones.

1,7-Di-(4-isopropylphenyl)-4-heptanone;
1,9-Diphenyl-5-nonanone;
1,5-Diphenyl-3-pentanone;
1,3-Diphenylacetone;
1,3-Di-(4-isopropylphenyl)acetone;
1,7-Diphenyl-4-heptanone;
1,3-Di-(4-t-butylphenyl)acetone;
1,7-Di-(4-ethylphenyl)-4-heptanone;
1,7-Di-(2-methyl-5-t-butylphenyl)-4-heptanone;
1,5-Di-(2-isopropylphenyl)-3-pentanone;
1,5-Di-(2,4,6-trimethylphenyl)-3-pentanone;
1,9-Di-(2-ethylphenyl)-5-nonanone;
1,5-Di-(4-t-butylphenyl)-3-pentanone;
1,5-Di-(4-methylphenyl)-3-pentanone;
1,7-Di-(4-t-butylphenyl)-4-heptanone.

PREPARATION B

Preparation of 4-Phenyl-1-(4-isopropylphenyl)-butanone-2

A Grignard reagent was prepared from 2-phenylethyl bromide 21 gm. (0.11 mole) and magnesium, 2.4 g. (0.1 gram atom). The magnesium is covered with 25 ml. of anhydrous ether, a crystal of iodine added and in a nitrogen atmosphere, the halide dissolved in 50 ml. of anhydrous ether is added, once initial reaction is obtained, at reflux temperature over a period of 1-2 hours. After complete addition, refluxing is continued for ½ hour.

In a nitrogen atmosphere, the Grignard solution is clarified by passage through a glass wool filter plug and added slowly to an agitated solution of 4-isopropylphenylacetonitrile, 14.9 gm. (0.09 mole) in 200 ml. of anhydrous diethyl ether. A gentle reflux is maintained during the addition which requires ½ to 1 hour. After complete addition and an additional 15 minutes at reflux, the reaction mixture is cooled and poured onto a mixture of 50 ml. of concentrated hydrochloric acid and 200 gms. of ice using good mixing. Upon warming the ether is removed by distillation and the residue heated at 70°-100° C. for 1 hour. The product is extracted with two portions, 250 ml. each of ether, the ether solution dried over anhydrous magnesium sulfate and the solvent removed. Any of the reactants, i.e., halide and nitrile, are separated from the ketone by fractional distillation under reduced pressure along with by-products.

In a similar procedure, the following ketones are prepared:

1-(2-Methylphenyl)-4-phenylpentan-2-one;

1-(4-t-Butylphenyl)-5-(4-isopropylphenyl)-pentan-3-one;
2-(3-Methylphenyl)-8-(2-isopropylphenyl)-octan-4-one;
1-(3-Methylphenyl)-4-(4-n-butylphenyl)-2-pentanone;
1,4-Di-(4-isopropylphenyl)-2-butanone;
1-Phenyl-3-(4-t-butylphenyl)acetone;
1-(3,4-Dimethylphenyl)-5-(4-isopropylphenyl)-3-pentanone;
2,6-Diphenyl-4-heptanone.

EXAMPLE 1

Preparation of 1-[1,5-Di-(4-isopropylphenyl)-3-pentyl]-1,5,9-triazanone 1,5-Di-(4-isopropylphenyl)-3-pentanone (12.88 g., 0.04 mole) and 3,3'-iminobispropylamine (26.2 g., 0.20 mole) in 250 ml. toluene is heated at reflux overnight with a Dean-Stark water separator. The cooled solution is concentrated under reduced pressure. The residue is dissolved in ethanol and hydrogenated with 1.5 g. $PtO_2$ at room temperature and 40 psi hydrogen pressure. The platinum catalyst is filtered off and the ethanol removed under vacuum. The residual oil is dissolved in ether and the ether solution washed several times with water to remove the excess 3,3'-iminobispropylamine. The ether extracts are dried over anhydrous sodium sulfate and concentrated under vacuum to leave the polyamine as a colorless oil.

The oil is dissolved in ether and hydrogen chloride gas is bubbled into the solution until no further precipitation occurs. The ether is evaporated under reduced pressure to leave the product as a solid which is digested with hot isopropyl alcohol. The solids are collected by filtration and dried under vacuum at 70° C. to give a colorless product, 1-[1,5-di-(4-isopropylphenyl)-3-pentyl]-1,5,9-triazanone trihydrochloride, m.p. 265° C.–267° C.

In an analogous manner from the ketones and the amines set forth below, there are prepared the following compounds of this invention.

TABLE II

| Ketone | Amine | Product | M.P. ° C. |
|---|---|---|---|
| 1,7-Di-(4-t-butylphenyl)-4-heptanone | N,N'-bis-(3-aminopropyl)-1,3-propanediamine | 1-[1,7-Di-(4-t-butylphenyl)-4-heptyl]-1,5,9,13-tetraazatridecane tetrahydrochloride | 258°–259° C. |
| 1,7-Di-(2-methyl-5-t-butylphenyl)-4-heptanone | N,N'-bis-(3-aminopropyl)-1,3-propanediamine | 1-[1,7-Di-(2-methyl-5-t-butylphenyl)-4-heptyl]-1,5,9,13-tetraazatridecance tetrahydrochloride | 259°–260° C. |
| 1,5-Di-(4-methylphenyl)-3-pentanone | 3,3'-Iminobis(propylamine) | 1-[1,5-Di-(4-methylphenyl)-3-pentyl]-1,5,9-triazanonane trihydrochloride | — |
| 1,5-Di-(2,4,6-trimethylphenyl)-3-pentanone | 3,3'-Iminobis(propylamine) | 1-[1,5-Di-(2,4,6-trimethylphenyl)-3-pentyl]-1,5,9-triazanonane trihydrochloride | 258°–260° C. |
| 1,7-Di-(4-t-butylphenyl)-4-heptanone | 3,3'-Iminobis(propylamine) | 1-[1,7-Di-(4-t-butylphenyl)-4-heptyl]-1,5,9-triazanonane trihydrochloride | 246°–247° C. |
| 1,7-Di-(2-methyl-5-t-butylphenyl)-4-heptanone | 3,3'-Iminobis(propylamine) | 1-[1,7-Di-(2-methyl-5-t-butylphenyl)-4-heptyl]-1,5,9-triazanonane trihydrochloride | 255°–257° C. |
| 1,7-Di-(4-isopropylphenyl)-4-heptanone | 3,3'-Iminobis(propylamine) | 1-[1,7-Di-(4-isopropylphenyl)-4-heptyl]-1,5,9-triazanonane trihydrochloride | 237°–239° C. |
| 1,7-Di-(4-t-butylphenyl)-4-heptanone | 1,3-Diamino-2-propanol | 1-[1,7-Di-(4-t-butylphenyl)-4-heptyl]-3-hydroxy-1,5-diazapentane dihydrochloride | 267°–269° C. |
| 1,5-Di-(4-t-butylphenyl)-acetone | 3,3'-Iminobis(propylamine) | 1-[1,5-Di-4-t-butylphenyl)-3-pentyl]-1,5,9-triazanonane trihydrochloride | 274°–275° C. |
| 1,7-Di-(4-isopropylphenyl)-4-heptanone | Triethylenetetramine | 1-[1,7-Di-(4-isopropylphenyl)-4-heptyl]-1,4,7,10-tetraazadecane tetrahydrochloride | 250°–252° C. |
| 1,7-Di-(4-t-butylphenyl)-4-heptanone | Triethylenetetramine | 1-[1,7-Di-(4-t-butylphenyl)-4-heptyl]-1,4,7,10-tetraazadecane tetrahydrochloride | 275°–276° C. |
| 1,7-Di-(2-methyl-5-t-butylphenyl)-4-heptanone | Triethylenetetramine | 1-[1,7-Di-(2-methyl-5-t-butylphenyl)-4-heptyl]-1,4,7,10-tetrazadecane tetrahydrochloride | 272°–274° C. |
| 1,5-Di-(4-isopropylphenyl)-3-pentanone | Triethylenetetramine | 1-[1,5-Di-(4-isopropylphenyl)-3-pentyl]-1,4,7,10-tetraazadecane tetrahydrochloride | 269°–270° C. |
| 1,3-Di-(4-Isopropylphenyl)-acetone | Triethylenetetramine | 1-[1,3-Di-(4-isopropylphenyl)-2-propyl]-1,4,7,10-tetraazadecane tetrahydrochloride | — |
| 1,3-Di-(4-t-butylphenyl)-acetone | Triethylenetetramine | 1-[1,3-Di-(4-t-butylphenyl)-2-propyl]-1,4,7,10-tetraazadecane tetrahydrochloride | |
| 1,3-Di-(4-isopropylphenyl)acetone | 3,3'-Iminobis(propylamine) | 1-[1,3-Di-(4-isopropylphenyl)-2-propyl]-1,5,9-triazanonane trihydrochloride | |
| 1,3-Di-(4-t-butylphenyl)-acetone | 3,3'-Iminobis(propylamine) | 1-[1,3-Di-(4-t-butylphenyl)-2-propyl]-1,5,9-triazanonane trihydrohydrochloride | |
| 1,9-Diphenyl-5-nonanediphenyl | N,N'-bis-(3-aminopropyl)-1,3-propanediamine | 1,9-Diphenyl-5-nonyl-1,5,9,13-tetrazatridecane tetrahydrochloride | |
| 1,5-Diphenyl-3-pentanone | 3,3'-Iminobis(propylamine) | 1,5-Diphenyl-3-pentyl-1,5,9-triazanonane trihydrobromide | |
| Dibenzylketone | 3,3'-Iminobis(propylamine) | 1,3-Diphenyl-2-propyl-1,5,9,13-tetrazatridecane tetrahydrochloride | |
| 1,7-Diphenyl-4-heptanone | 3,3'-Iminobis(propylamine) | 1,7-Diphenyl-4-heptyl-1,5,9-triazanonane trihydrochloride | |
| 1,7-Di-(4-ethylphenyl)-4-heptanone | 1,3-Diamino-2-propanol | 1,7-Di-(4-ethylphenyl)-4-heptyl-3-hydroxy-1,5-diazapentane dihydrochloride | |

TABLE II-continued

| Ketone | Amine | Product | M.P. ° C. |
|---|---|---|---|
| 1,5-Di-(2-isopropylphenyl)-3-pentanone | 3,3'-Iminobis(propylamine) | 1,5-Di-(2-isorpopylphenyl)-3-pentyl-1,5,9-triazanonane trihydrobromide | |
| 1,9-Di-(2-ethylphenyl)-5-nonanone | Triethylenetetramine | 1,9-Di-(2-ethylphenyl)-5-nonyl-1,4,7,10-tetraazadecane tetrahydrochloride | |
| 1-(3-Methylphenyl)-4-(4-n-butylphenyl)-2-pentanone | 3,3'-Methyliminobis(propylamine) | 1-[1-(3-Methylphenyl)-4-(4-n-butylphenyl)-2-pentyl]-5-methyl-1,5,9-triazanonane | |
| 1,4-Di-(4-isopropylphenyl)-2-butanone | Tris-(2-aminoethyl)amine | 1-[1,4-Di-(4-isopropylphenyl)-2-butyl]-4-(2-aminoethyl)-1,4,7-triazaheptane | |
| 1-Phenyl-3-(4-t-butylphenyl)-acetone | Dipropylenetriamine | N-[(1-Phenyl-3-(4-t-butylphenyl)-propyl]dipropylenetriamine | |
| 1-(3,4-Dimethylphenyl)-5-(4-isopropylphenyl)-3-pentanone | Spermine | 1-[1-(3,4-Dimethylphenyl)-5-(4-isopropylphenyl)-3-pentyl]-1,5,10,14-tetraazatetradecane | |
| 2,6-Diphenyl-4-heptanone | 1-(2-hydroxyethyl)-1,5,8-triazaoctane | 1-(2,6-Diphenyl-4-heptyl)-8-(2-hydroxyethyl)-1,4,8-triazaoctane | |
| Dibenzylketone | 1-(2-hydroxypropyl)-5-hydroxymethyl-1,5,9-triazanonane | 1-(1,3-Diphenyl-2-propyl)-5-hydroxymethyl-9-(2-hydroxypropyl)-1,5,9-triazanonane | |

EXAMPLE 2

Preparation of 1-[1,5-Di-(4-isopropylphenyl)-3-pentyl]-1,4,7,10-tetrazadecane 1,5-Di-(4-Isopropylphenyl)-3-pentanone (0.02 mole) and triethylenetetramine (0.10 mole) in 150 ml. of toluene is heated at reflux overnight with a Dean-Stark water separator. The toluene is then removed under vacuum. The residual oil dissolved in 25 ml. isopropanol is added dropwise to sodium borohydride (1.90 g., 0.05 mole, excess) suspended in 50 ml. isopropanol. After complete addition, the reaction mixture is heated at reflux for one hour. The isopropanol is evaporated under reduced pressure, the residue treated with water and the aqueous mixture extracted well with ether. The combined ether extracts are back-washed with water, a saturated sodium chloride solution, dried over anhydrous sodium sulfate and concentrated under vacuum to leave the polyamine product as a clear oil 7.4 g. (90%).

The oil is dissolved in ether and the solution cooled in an ice-water bath. Hydrogen chloride gas is bubbled into the solution until no further precipitate is formed. The solid is collected by filtration, washed with a small amount of ether, and dried under vacuum to leave the polyamine tetrahydrochloride as a colorless product.

EXAMPLE 3

1-[1,7-Di-(4-Methylphenyl)-4-heptyl]-1,4,8-triazaoctane

A mixture of 1,7-di-(4-methylphenyl)-4-heptanone (0.03 mole) and 1,2-diaminoethane (12.0 g., 0.20 mole) in 250 ml. ethanol is heated at reflux overnight. The cooled reaction mixture is hydrogenated with $PtO_2$ at room temperature and 40 psi hydrogen pressure. The platinum catalyst is filtered off and the ethanol removed under reduced pressure. The residual oil is dissolved in ether and the ether solution washed several times with water to remove the excess diaminoethane. The ether extracts are dried over anhydrous sodium sulfate and concentrated under vacuum to leave a colorless oil, 11.2 g. (100%).

The oil is dissolved in 20 ml. tert-butanol and chilled to 0° C.–5° C. in an ice-water bath. Acrylonitrile (1.75 g., 2.2 ml., 0.033 mole) is added dropwise over a 5-minute period. The reaction mixture is allowed to warm up to room temperature and is then heated at 60° C. overnight. The t-butanol was removed under reduced pressure. The residual oil was dissolved in 150 ml. glacial acetic acid and hydrogenated with $PtO_2$ at room temperature and 40 psi hydrogen pressure. The platinum catalyst is filtered off and the acetic acid removed under vacuum. The residue is dissolved in ether and made basic with 10% sodium hydroxide. The ether solution is washed with water, dried over anhydrous sodium sulfate and concentrated under reduced pressure.

In addition to the compounds specifically set forth in the foregoing examples, each of the respective ketones set forth in Preparations A and B when reacted with the individual amines set forth in the foregoing specification especially at pages 10 and 11 according to the method set forth in Example I produce the entire range of compounds described according to this invention as embodied in Formula I.

What is claimed is:

1. An antibacterial composition comprising an admixture of 1 to 500 parts by weight of tris(hydroxymethyl)aminomethane for each part by weight of a polyamine having the formula:

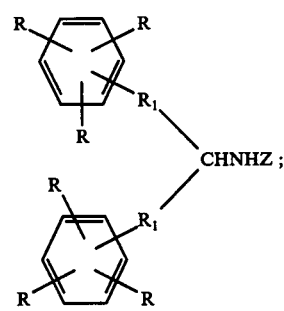

(2)

where
R is hydrogen or loweralkyl;
each $R_1$ is alike or different and is $C_1$ to $C_4$ alkylene;
Z is

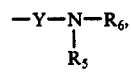

where
Y is

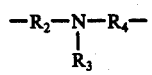

or Y is —R$_2$— and

R$_2$ is 2-hydroxy-1,3-trimethylene, or R$_1$ as previously defined;

R$_3$ is hydrogen, C$_1$ to C$_4$ alkyl, C$_2$ to C$_4$ aminoalkyl, C$_1$ to C$_4$ hydroxyalkyl, or C$_2$ to C$_4$ dihydroxyalkyl;

R$_4$ is 2-hydroxy-1,3-trimethylene, or R$_1$ as previously defined;

R$_5$ is hydrogen, aminoethyl, aminopropyl, C$_1$ to C$_4$ hydroxyalkyl, or C$_2$ to C$_4$ dihydroxyalkyl; and R$_6$ is hydrogen, C$_1$ to C$_4$ hydroxyalkyl or C$_2$ to C$_4$ dihydroxyalkyl;

or when R$_3$ and R$_6$ taken together are ethylene, R$_4$ is also ethylene, and R$_5$ is aminoethyl, aminopropyl, or aminohydroxypropyl or acid addition salts thereof.

2. The composition according to claim 1 where R$_1$ is methylene.

3. The composition according to claim 1 where R$_1$ is ethylene.

4. The composition according to claim 1 where R$_1$ is trimethylene.

5. The composition according to claim 1 where Z is

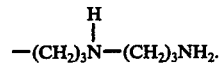

6. The composition according to claim 1 where Z is —(CH$_2$)$_2$NH$_2$.

7. The composition according to claim 1 where Z is

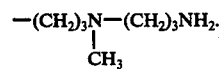

8. The composition according to claim 1 where Z is —CH$_2$CHOHCH$_2$NH$_2$.

9. The composition according to claim 1 where Z is —(CH$_2$)$_3$NH$_2$.

* * * * *